US011628239B2

(12) United States Patent
Akins et al.

(10) Patent No.: US 11,628,239 B2
(45) Date of Patent: Apr. 18, 2023

(54) METHOD FOR PROTECTING SKELETONIZED BLOOD VESSELS

(71) Applicants: University of Delaware, Newark, DE (US); The Nemours Foundation, Jacksonville, FL (US)

(72) Inventors: Robert Akins, West Chester, PA (US); Kristi L. Kiick, Rising Sun, MD (US); Karyn Robinson, Wilmington, DE (US); Rebecca Scott, Newark, DE (US)

(73) Assignees: University of Delaware, Newark, DE (US); The Nemours Foundation, Jacksonville, FL (US)

( * ) Notice: Subject to any disclaimer, the term of this patent is extended or adjusted under 35 U.S.C. 154(b) by 141 days.

(21) Appl. No.: 16/344,115

(22) PCT Filed: Nov. 3, 2017

(86) PCT No.: PCT/US2017/060009
§ 371 (c)(1),
(2) Date: Apr. 23, 2019

(87) PCT Pub. No.: WO2018/102074
PCT Pub. Date: Jun. 7, 2018

(65) Prior Publication Data
US 2020/0061244 A1  Feb. 27, 2020

Related U.S. Application Data

(60) Provisional application No. 62/417,688, filed on Nov. 4, 2016.

(51) Int. Cl.
*A61L 31/08* (2006.01)
*A61L 27/36* (2006.01)
*A61L 27/52* (2006.01)
*A61L 27/54* (2006.01)

(52) U.S. Cl.
CPC ........... *A61L 27/3625* (2013.01); *A61L 27/52* (2013.01); *A61L 27/54* (2013.01); *A61L 2300/236* (2013.01); *A61L 2300/41* (2013.01); *A61L 2300/414* (2013.01); *A61L 2300/416* (2013.01); *A61L 2300/426* (2013.01); *A61L 2300/626* (2013.01); *A61L 2420/06* (2013.01)

(58) Field of Classification Search
None
See application file for complete search history.

(56) References Cited

U.S. PATENT DOCUMENTS

| | | | | |
|---|---|---|---|---|
| 2003/0087878 A1* | 5/2003 | Vinten-Johansen | ...... | A61P 9/00 514/56 |
| 2004/0044405 A1 | 3/2004 | Wolff et al. | | |
| 2005/0165427 A1* | 7/2005 | Jahns | ............... | A61B 17/32053 606/153 |
| 2010/0074934 A1 | 3/2010 | Hunter | | |
| 2010/0198241 A1 | 8/2010 | Gerrah et al. | | |
| 2010/0256746 A1* | 10/2010 | Taylor | ...................... | B05D 3/12 623/1.42 |
| 2011/0077216 A1 | 3/2011 | Kastrup et al. | | |
| 2011/0190572 A1 | 8/2011 | Brophy et al. | | |
| 2014/0277070 A1* | 9/2014 | Otero | ................. | A61B 17/1219 606/194 |
| 2016/0058913 A1* | 3/2016 | Dimitrievska | ......... | A61L 33/08 427/2.25 |

FOREIGN PATENT DOCUMENTS

WO  99/45852 A2  9/1999

OTHER PUBLICATIONS

International Preliminary Report on Patentability and Written Opinion for International Application No. PCT/US2017/060009, dated May 7, 2019, 7 pages.
Daly et al., J Thorac Cardiovasc Surg 96(1):19-29.
De Menezes et al., Braz J. Cardiovasc 2007, 22(2):206-211.
Feeney et al., Modification of Proteins; Advances in Chemistry Series, vol. 198, American Chemical Society, Washington, D.C., 1982.
Ghazanfari, et al., Biochem Biophys Res Commun 426(1):54-58 (2012).
Mamchur et al., Semin Thorac Cardiovasc Surg 27(2):115-120, 2015.
March Advanced Organic Chemistry, 6th Ed., John Wiley & Sons, New York, 2007—2374 pages.
Reardon et al., J Cardiovasc Surg (Torino) 38(3):201-209, 1997.
Ruengsakulrach et al., Circulation 100 (19 Suppl): II 139-144, 1999.
Sa et al., Int J Surg 12(7):666- 672, 2014.
Angouras et al., Eur J Cardio-thoracic Surg, 17:468-473 (2000).
Del Campo, Tex Heart Inst J, 30(3):170-5 (2003).
Epstein et al., JAMA, 305(17):1769-76 (2011).
International Search Report for PCT Application No. PCT/US2017/060009 dated May 15, 2018 by Lee W. Young.
Joseph et al., Circ Res, 121:677-94 (2017).
Lau et al., ACS Biomater. Sci. Eng., pp. A-J (2016).
Leong et al., Circ Res, 121:695-710 (2017).
Liang and Kiick, Biomacromolecules, 17:601-14 (2016).
Maruyama et al., Heart Vessels, 31:474-81 (2016).
Riley et al., Circulation Cardiovascular Quality and Outcomes, 4:193-7 (2011).
Robinson et al., Bioengineering & Translational Medicine, 2:222-32 (2017).

(Continued)

Primary Examiner — Susan T Tran
(74) Attorney, Agent, or Firm — RatnerPrestia (57) ABSTRACT

Skeletonized blood vessels for use as vascular grafts are protected from biomechanical injury and/or certain cellular and extracellular changes by application of a biocompatible hydrogel to the vessel exterior. The hydrogel may be applied to the vessel graft before or after harvesting from a donor patient.

20 Claims, 4 Drawing Sheets

(56) References Cited

OTHER PUBLICATIONS

Scott et al., Biomaterials, 137:1-10 (2017).
Sergeant et al., Ann Thorac Surg, 66(1):1-11 (1998).
Shruthi et al., Stem Cells in PEG Hydrogel for Vascular Graft Repair, Critical Care Medicine 2013 (Abstract).
Toeg et al., J Thorac Cardiovasc Surg, 147:4-5 (2014).

* cited by examiner

METHOD FOR PROTECTING SKELETONIZED BLOOD VESSELS

CROSS-REFERENCE TO RELATED APPLICATION

This application is a U.S. national phase of International Application No. PCT/US2017/060009, filed Nov. 3, 2017, claiming priority to U.S. Provisional Application No. 62/417,688, filed Nov. 4, 2016, the entire disclosure of each of which is incorporated herein by reference in its entirety for all purposes.

This invention was made with government support under Grant No. R01HL108110 awarded by the National Institutes of Health. The government has certain rights in the invention.

FIELD OF THE INVENTION

The invention relates to surgery and the manipulation of blood vessels. In particular, the invention relates to methods for attenuation of the negative effects of vascular skeletonization.

BACKGROUND OF THE INVENTION

Cardiovascular diseases are leading causes of morbidity and mortality worldwide with coronary, peripheral, and congenital vascular diseases remaining major health problems. (Leong, D. P., et al. *Circ Res* 121, 695-710, 2017; Joseph, P., et al. *Circ Res* 121, 677-694, 2017). Principal treatments include angioplasty to open blockages and surgery to place bypass grafts. Similar approaches are employed in the treatment of arterial diseases, congenital cardiovascular malformations, and the maintenance of vascular access for dialysis. Coronary arterial disease, in particular, is a significant problem. Despite the revolutionizing impact of angiography, angioplasty, and stenting, bypass surgery continues to be a critical treatment option; however, complications associated with grafting procedures remain significant problems. (Epstein, A. J., et al. *JAMA* 305, 1769-1776, 2011; Riley, et al. *Circulation. Cardiovascular Quality and Outcomes* 4, 193-197, 2011). In all cases of vascular manipulation, maladaptative responses in the manipulated vessels can result in fibrosis, stenosis, and vessel failure. Approaches that attenuate the negative effects of surgical manipulation, especially in coronary artery bypass grafting (CABG), are needed.

Although vein to artery grafting remains a standard approach, superior long-term patency in CABG has been achieved using arterial grafts. Internal thoracic artery (ITA) approaches were reported in the 1990s (Reardon et al., *J Cardiovasc Surg (Torino)* 38(3): 201-209, 1997); more recently, the radial artery (RA) has become the second choice of conduits following the ITA (Maruyama et al., *Heart Vessels* 31(4): 474-481, 2016).

There are two established harvesting techniques for coronary arterial grafts: pedicled and skeletonized. For example, in pedicled techniques involving the ITA, the artery is dissected away from the sternum with its accompanying veins, fascia, adipose tissue, and lymphatics. In skeletonization, the artery is dissected free of all surrounding tissue, solely yielding the artery (Sa et al., *Int J Surg* 12(7): 666-672, 2014). Skeletonization has distinct advantages and disadvantages.

The reported benefits of skeletonized harvesting include increased graft flow, increased graft length, decreased incidence of mediastinitis, and the reduction in postoperative pain. The method of internal thoracic artery (ITA) harvesting for coronary artery bypass graft surgery has also been shown to influence the incidence of post-operative sternal wound infection, and result in shorter hospital stays, less chest pain, and fewer superficial infections. For these reasons, the skeletonization method of harvesting has increased in popularity and is the preferred method of many surgeons.

Despite the benefits of skeletonization and its surgical popularity, skeletonization of the ITA has been associated with long-term atherosclerosis risk (Del Campo, *Tex Heart Inst J* 30(3): 170-175, 2003), and if the ITA is partially denuded of the adventitium and vasa vasorum during skeletonization, areas of vessel degeneration develop (Id.). In studies using a canine model, skeletonized ITAs stripped of their adventitia had higher incidences of thrombosis, intimal thickening, and medial injury than did free ITA grafts with pedicles (Daly et al., *J Thorac Cardiovasc Surg* 96(1): 19-29, 1988). It has been shown in an experimental model that interruption of the vasa vasorum of the aorta leads to abnormal morphology of elastin and collagen fibers of the outer media, which resulted in increased arterial wall stiffness within 15 days (Angouras et al., *Eur J Cardiothorac Surg* 17(4): 468-473, 2000).

Another serious problem of early graft failure results from vasospasm, which can cause graft occlusion and intimal hyperplasia (Sergeant et al., *Ann Thorac Surg* 66(1): 1-10, 1998; Ruengsakulrach et al., *Circulation* 100 (19 Suppl): II 139-144, 1999, Del Campo, supra).

Mechanical injury during harvesting is considered one of the main mechanisms predisposing to ITA and RA spasms (Mamchur et al., *Semin Thorac Cardiovasc Surg* 27(2): 115-120, 2015). Thus, although ITA skeletonization allows increasing the graft's length and decreasing the sternal ischemia, it may result in unseen damage to the artery wall (Toeg and Rubens, *J Thorac Cardiovasc Surg* 147(1): 4-5, 2014) and subsequent maladaptive responses by the vessel. Mamchur et al. (supra) found degenerative changes in 56% of skeletonized human ITAs and 74% of skeletonized human radial arteries compared to 30% of pedicled ITAs and 41% of pedicled RAs. Changes associated with vessel skeletonization in these studies included splitting of internal elastic laminae, reduced tortuosity of the internal elastic laminae, and thickening and detachment of the intima. Approaches that can attenuate these negative effects are needed.

What is needed is a modality that allows the benefits of skeletonization to be realized without the associated negative effects. In particular, a means of protecting skeletonized blood vessels against biomechanical, cellular, and extracellular changes is needed.

SUMMARY OF THE INVENTION

A method for protecting a skeletonized blood vessel comprises forming a coating comprising a biocompatible hydrogel on at least a portion of an outer surface of the blood vessel.

In some embodiments, the vessel is a vein. In other embodiments, the vessel is an artery.

The blood vessel may be selected from the group consisting of aortas, carotid arteries, coronary arteries, internal mammary arteries, internal thoracic arteries, radial arteries, femoral arteries, gastroepiploic arteries, popliteal arteries, and saphenous veins. The blood vessel may be an internal thoracic artery. The blood vessel may be a saphenous vein. The blood vessel may be a radial artery. The blood vessel may be a gastroepiploic artery.

In some embodiments, the skeletonized blood vessel is present in the body of a donor and the method further comprises depositing the coating comprising the biocompatible hydrogel on the outer surface of the blood vessel in the body of the donor before harvesting.

Where the skeletonized blood vessel is harvested from a donor, the method may further comprise depositing the coating on the outer surface of the blood vessel in the donor before harvesting. The donor may be a patient who receives the protected skeletonized vessel.

In some embodiments, the coating comprising the biocompatible hydrogel is deposited on the vessel after harvesting of the blood vessel. In some embodiments, the coating comprising the biocompatible hydrogel is formed on outer surface of the blood vessel and the method further comprises delivering to the outer surface of the blood vessel a composition comprising two or more hydrogel precursor reactants that react to form the hydrogel coating on the outer surface of the blood vessel.

In one embodiment of the method, the two or more hydrogel precursor reactants comprise a first hydrogel precursor reactant and a second hydrogel precursor reactant, and are delivered to the outer surface of the vessel by injection from a dual barrel syringe comprising a mixing chamber connected to a syringe chamber comprising a first barrel containing a first hydrogel precursor reactant and a second barrel containing a second hydrogel precursor reactant. The method further comprises mixing the first and second hydrogel precursor reactants in the mixing chamber during delivery.

In some embodiments, the coating covers at least about 50%, 70%, 75%, 80%, 90%, 95%, 99% or 100% of the length of the blood vessel.

In some embodiments, the coating on the outer surface of the blood vessel has a thickness in the range of from about 0.25 mm to about 5 mm.

In certain embodiments, the hydrogel comprises a cross-linked polymer network formed by reaction of a first functionalized base polymer comprising at least two first reactive groups and a second functionalized base polymer comprising at least two second reactive groups, the second reactive groups being reactive with the first reactive groups, thereby forming the cross-linked polymer network. The first and second functionalized base polymers may be hydrophilic.

The first and second functionalized base polymers may form a microstructured network. The microstructured network may comprise domains with average diameters ranging from 0.1 to 1000 microns or ranging from 10 to 500 microns.

In some embodiments, the first and second functionalized base polymers in the hydrogel have a concentration of from about 1 to about 20 wt %, for example, from about 4 to about 7 wt % or from about 4 to about 6 wt %.

The hydrogel may have a modulus of from about 600-13,000 Pa, for example, about 750-12,500 Pa, about 1,000-12,500 Pa, about 1,000-10,000 Pa, about 2,500-10,000 Pa or 4,000-8,000 Pa.

The cross-linked polymer network may include a heterogeneous component, in addition to other components such as the reaction products of the above-mentioned first and second functionalized polymers. The heterogeneous component may be selected from the group consisting of liposomes, phase separated networks and combinations thereof.

The first reactive groups may comprise alkene moieties and the second reactive groups comprise thiol moieties. Thiol-maleimide pairs may be used.

The first reactive groups may comprise azide moieties and the second reactive groups may comprise alkyne moieties. The first reactive groups may comprise maleimide moieties and the second groups may comprise thiol moieties. The thiol moieties may comprise aryl thiols.

The first and second functionalized base polymers may be selected from the group consisting of polyethylene glycol, poly(ethylene oxide), poly(vinyl alcohol), poly(N-alkyl acrylamide)s, poly(ester)s, poly(N-vinylpyrrolidone), poly(vinyl acetate), proteins, polypeptides, peptides, polysaccharides, and copolymers, conjugates or mixtures thereof.

The first and second functionalized base polymers may be selected from the group comprising heparins and low molecular-weight heparins.

The first and second functionalized base polymers may be selected from the group comprising resilin-like polypeptides.

In certain embodiments, the first functionalized base polymer comprises $n_1$-arm-PEG-maleimide wherein $n_1$ is an integer from 2 to 20, preferably from 2 to 12, and the second functionalized base polymer comprises $n_2$-arm-PEG-SH wherein $n_2$ is an integer from 2 to 20, preferably from 2 to 12. In one embodiment, both $n_1$ and $n_2$ are 4.

The hydrogel may comprise an agent selected from the group consisting of peptides and small molecules. The small molecules may be anti-inflammatory compounds. The hydrogel may comprise vesicles, liposomes or lipids. The hydrogel may comprise sirolimus or rapamycin. The hydrogel may comprise heparin or low-molecular weight heparin. The hydrogel may comprise proteins, cytokines or growth factors. The hydrogel may comprise fibroblast growth factor.

In certain embodiments, the hydrogel may be a supramolecular or self-assembled hydrogel. In certain embodiments, the gel may be a peptide hydrogel. Peptide hydrogels can have very low wt %, towards the lower end of the ranges mentioned in the next paragraph.

In some embodiments, the gel-forming agent in the hydrogel has a concentration of from about 0.05 to about 50 wt %, preferably from about 1 to about 10 wt %, more preferably from about 3 to about 6 wt %, based on the weight of the hydrogel. The concentration may be at least about 0.05, 0.1, 0.25, 0.5, 1, 2, or 3 wt %, and may be up to about 6, 8, 10, 20, 25, 30, 40, or 50 wt %.

Any of those minima may be combined with any of those maxima as may be appropriate in a particular situation.

In another embodiment, a method for harvesting a skeletonized blood vessel from a donor comprises exposing a blood vessel in a donor, skeletonizing the exposed blood vessel, and forming a coating comprising a biocompatible hydrogel on at least a portion of an outer surface of the exposed blood vessel. The donor may be a patient who receives the harvested blood vessel. In different embodiments, the hydrogel may be added either before or after harvesting of the blood vessel.

In another embodiment, a composition comprises a skeletonized blood vessel and a hydrogel coating at least a portion of an outer surface of the blood vessel. In one embodiment, the skeletonized blood vessel is harvested from a donor.

In another embodiment, a method for treatment of a congenital cardiovascular malformation or a peripheral artery disease in a patient is provided. The method comprises placing in the patient the skeletonized blood vessel protected according to the method of the present invention or the blood vessel harvested according to the method of the present invention. Where the protected skeletonized blood vessel or the harvested skeletonized blood vessel is placed at an anastomotic site in the patient, the method may further comprise injecting or placing the biocompatible hydrogel to cover the anastomotic site.

In another embodiment, a method for maintenance of vascular access in a patient is provided. The patient is subject to dialysis or a surgery. The method comprises placing in the patient the skeletonized blood vessel protected according to the method of the present invention or the blood vessel harvested according to the method of the present invention. Where the protected skeletonized blood vessel or the harvested skeletonized blood vessel is placed at an anastomotic site in the patient, the method may further comprise injecting the biocompatible hydrogel to cover the anastomotic site.

As envisioned in the present invention with respect to the disclosed compositions of matter and methods, in one aspect the embodiments of the invention comprise the components and/or steps disclosed herein. In another aspect, the embodiments of the invention consist essentially of the components and/or steps disclosed herein. In yet another aspect, the embodiments of the invention consist of the components and/or steps disclosed herein.

BRIEF DESCRIPTION OF THE FIGURES

FIG. 4 also shows a graph of the number of elastic laminae present in sections of carotid from control, skeletonized, and skeletonized hydrogel-treated arteries (B), examples of elastin distribution patterns from the same control, skeletonized, and skeletonized hydrogel-treated arteries (C), images formed from forward and backward scatter second harmonic signals from collagen showing mature and immature fibers (D), and the normalized ratio of forward to backward scattered signals indicating a statistically-significant difference between skeletonized and control arteries (E). Mature collagen appears magenta in the original color image and newer collagen appears yellow in the original color image. Differences in the back versus forward patterns are indicative of new collagen formation and collagen turnover. These images represent a skeletonized, hydrogel-treated carotid.

DETAILED DESCRIPTION OF THE INVENTION

Definitions

Unless defined otherwise, all technical and scientific terms used herein have the same meaning as commonly understood by one of ordinary skill in the art to which the invention pertains.

Although any methods and materials similar or equivalent to those described herein can be used in the practice for testing of the present invention, the preferred materials and methods are described herein. In describing and claiming the present invention, the following terminology will be used. It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element. Thus, recitation of "a cell", for example, includes a plurality of the cells of the same type.

"About" as used herein when referring to a measurable value such as an amount, a temporal duration, and the like, is meant to encompass variations of +/−20% or +/−10%, more preferably +/−5%, even more preferably +/−1%, and still more preferably +/−0.1% from the specified value, as such variations are appropriate to perform the disclosed methods.

As used herein, "blood vessel" has its ordinary meaning in medicine and includes any of the vessels, such as arteries, veins, or capillaries, through which blood circulates. It is understood that the phrase "blood vessel" or "artery" or "vein" includes not only the anatomically full length vessel, but also a segment thereof comprising less than the full anatomical length. Thus, "blood vessel" or "artery" or "vein" is understood to also include segments of those vessels.

A "functionalized polymer" is a polymer which bears a reactive chemical group capable of reaction with another chemical group, such as a reactive chemical group on another functionalized polymer.

By "hydrogel" is meant a material comprising a molecular network that can absorb water and swell without dissolving, at least temporarily. The molecular network can be polymer, peptide, protein, polypeptide, polysaccharide, small-molecule. A "biocompatible hydrogel" is a hydrogel that in a given organism is compatible with living tissue or a living system by not being toxic or injurious and eliciting little or no immune response. Embodiments of the present hydrogels may react a little with the surrounding tissue, and that is not necessarily undesirable.

By "hydrogel precursor reactant" is meant a compound or substance which upon reaction with another compound or substance results in the formation of a network which, upon absorption of water, functions as a hydrogel.

As used herein, "individual," "donor," or "patient" or "subject" (as in the subject of the treatment) means both mammals and non-mammals. Mammals include, for example, humans; non-human primates, e.g. apes and monkeys; cattle; horses; sheep; and goats. Non-mammals include, for example, fish and birds. The individual is, in one embodiment, a human being. A donor is an individual from who a blood vessel may be harvested. A patient or subject is an individual in whom a blood vessel, for example, a protected skeletonized blood vessel, is placed. A donor may be a patient or subject.

By "skeletonized" as applied to a blood vessel is meant a vessel that has been dissected free of all or substantially all surrounding tissue. A skeletonized blood vessel is contrasted with a pedicled blood vessel. The skeletonized blood vessel may comprise the blood vessel at more than 90, 95, 99 or 99.5 wt % of the total weight of the skeletonized blood vessel.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Embodiments of the present invention are described below. It is, however, expressly noted that the present invention is not limited to these embodiments, but rather the intention is that modifications that are apparent to the person skilled in the art and equivalents thereof are also included.

According to the present invention, skeletonized blood vessels are protected during and after harvesting from biomechanical injury and/or certain cellular and extracellular changes by application of a biocompatible hydrogel to the vessel exterior. Hydrogel application has been found to prevent the decrease in circumferential strain that may accompany vessel skeletonization. In some subjects where vessel skeletonization resulted in increase of the vessel intimal-medial thickness, a hypertrophic/atherosclerotic response to the skeletonization, application of hydrogel was found to diminish this response. Application of hydrogel was also found to block vessel medial elastin reduction and intact vessel laminae reduction, which are further adverse effects of skeletonization.

The hydrogel may be applied to the external surface of a skeletonized vessel by any means that does not adversely affect the biomechanical or biological integrity of the vessel. For example, the hydrogel may be applied to the vessel by swabbing, dousing, injection from a syringe or syringe-like device, or any other method that results in the application of a hydrogel coating to at least a portion of the exterior surface of the vessel.

Preferably, the hydrogel is deployed completely around the entire exterior circumference of the vessel, across the full extent of the skeletonized portion, i.e., the entire skeletonized surface of the vessel is preferably covered by a hydrogel coating. The hydrogel may also be applied to a portion of the skeletonized vessel surface.

According to a preferred embodiment, hydrogel formation occurs simultaneously or near simultaneously upon instillation of a mixture of hydrogel precursor reactants at the vessel surface. This results in application of a freshly-formed hydrogel to the target vessel, and minimizes hydrogel deterioration that may accompany attempts to apply a pre-formed hydrogel to the vessel surface. Accordingly, two or more hydrogel precursor reactants, at least one of which is contained in an aqueous solution as a source of water for hydrogel formation, are mixed and immediately deposited on the vessel surface.

According to one embodiment, co-administration of two preferably aqueous solutions of hydrogel precursor reactant may be taken up in the separate containment chambers of a double-barrel syringe of other suitable dual-chamber delivery device that keeps the two solutions apart until application. The delivery device preferably further contains a mixing chamber in fluidic communication with the containment chambers. In a double-barrel syringe device, the mixing chamber is located at the tip of the device. Alternatively, the mixing chamber may be separate from the delivery device, so long as there is fluidic communication between the mixing chamber and containment chambers.

According to one embodiment, two solutions of different hydrogel precursor reactant solutions held in the respective chambers of a double-barrel syringe or syringe-like device are forced through the syringe mixing chamber and deposited on the vessel surface. It may be appreciated that according to this embodiment, hydrogel formation begins to occur in the mixing chamber upon initial mixing of the hydrogel precursor reactant solutions, and may continue as the mixture is deposited on the vessel. According to certain embodiments, hydrogel formation proceeds over a period of 5 seconds to 5 minutes, more typically from 5 to 30 seconds, and possibly as little as 5-15 seconds, or even less. A supramolecular or self-assembling hydrogel, for example, could re-form immediately (essentially instantaneously) after injection from the syringe.

According to another embodiment, the hydrogel may be applied to the vessel surface by applying a first solution of a first hydrogel precursor reactant, followed by application of a second solution of a second hydrogel precursor reactant, the hydrogel thus forming in situ on the vessel surface.

It should be appreciated that the foregoing techniques for application of hydrogel to a skeletonized vessel exterior surface may be practiced on an excised skeletonized vessel already harvested from a donor, or may be practiced on a skeletonized vessel that is surgically exposed but still present in the body of the donor. The latter is the preferred practice, as the protective effect of the hydrogel will minimize damage to the vessel during the harvesting process.

Upon application of hydrogel to the exposed skeletonized vessel of the vessel donor, the hydrogel-protected vessel is harvested by well-known harvesting techniques. It may be appreciated that the harvested vessel may be used for forming a graft in the body of the same subject (autologous graft) or in another subject.

The skeletonized vessel for treatment according to the present invention may be any vein or artery that is useful as a surgical graft. Veins include, for example, the saphenous vein. Arteries include, for example, the left internal thoracic artery, right internal thoracic artery, radial artery, right gastroepiploic artery, inferior epigastric artery, splenic artery, aorta, carotid artery, coronary artery, internal mammary artery, femoral artery, and popliteal artery. Vessels can be skeletonized according to known surgical techniques. For a detailed protocol for skeletonization of the internal thoracic artery, see for example, de Menezes et al., *Rev Bras Cir Cardiovasc* 22(2) São José do Rio Preto April/June 2007.

The hydrogel applied to the skeletonized vessel surface should have a thickness sufficient to form a layer around the circumference of the vessel exterior or, in the case of a vessel remaining in the body of the donor, as much of the vessel exterior as is readily accessible. Under some circumstances, it may be desirable to coat only a segment of the entire skeletonized vessel. The thickness of the hydrogel coating may vary, for example, from about 0.25 mm to about 5 mm. Other thicknesses are possible.

The concentration of gel-forming agent in the hydrogels of the present invention may vary considerably, but typically will comprise from about 0.005 to about 50 wt %, preferably up to about 25 wt %, more preferably from about 0.1 to about 10 wt %, based upon the weight of the hydrogel. Where the hydrogels are aqueous compositions of polymers, the hydrogel may advantageously comprise from about 1 to about 9 wt %, from about 2 to about 8 wt %, from about 3 to about 7 wt %, or from about 3 to about 6 wt %, polymer. Particular polymer concentrations are 1, 2, 3, 4, 5, 6, 7, 8, 9 or 10%.

It may be appreciated that the concentration of the polymer in the hydrogel may be adjusted, for example, by adjusting the concentration of the hydrogel precursor reactant solutions combined to form the hydrogel.

The hydrogel is preferably applied to the skeletonized vessel as soon as possible following skeletonization, in order to minimize the biomechanical, cellular and extracellular changes that take place in the vessel as a result of the skeletonization process. In any event, the hydrogel is preferably applied at least before a skeletonized vessel is harvested to minimize damage, although it is possible to apply the hydrogel coating to an already harvested skeletonized vessel.

In some embodiments, the graft may be stored in hydrogel. Some embodiments of the hydrogel would be able to remain intact on re-grafting, and may stay on the vessel when it is re-grafted.

The hydrogel may comprise any biocompatible polymer suitable for contact with mammalian tissue. Biocompatibility of hydrogel-forming materials and hydrogels, particularly compatibility with blood vessels, may be tested according to known techniques, such as the aortic fibroblast cell culture described in Example 1, below. Non-limiting examples of hydrogel-forming polymers that are relevant for biomedical applications are primarily hydrophilic polymers such as polyvinyl alcohol, polyethylene-glycol, polysaccharides, polylactic acids and their copolymers, and polypeptides and proteins. Some peptides and some small-molecule hydrogelators can also be gel-forming.

In certain embodiments, hydrogels are formed by methods from functionalized base polymers, using crosslinking chemistries known by those skilled in the art. Hydrogel-forming base polymers include, for example, dextran (DEX), polyethylene glycol (PEG) and poly(vinyl alcohol) (PVA) that have been functionalized to provide cross-linking sites. Reactive functional groups and classes of reactions useful in covalent linking and cross-linking are generally known in the art. These include, but are not limited to nucleophilic substitutions (e.g., reactions of amines and alcohols with acyl halides and activated esters), electrophilic substitutions (e.g., enamine reactions) and additions to carbon-carbon and carbon-heteroatom multiple bonds (e.g., Michael reactions, Diels-Alder reactions, photocatalyzed thiol-ene chemistries, photoinitiated reactions, and enzymatic reactions). These and other useful reactions are discussed, for example, in: March, *Advanced Organic Chemistry*, 3rd Ed., John Wiley & Sons, New York, 1985; Hermanson, *Bioconjugate Techniques*, Academic Press, San Diego, 1996; and Feeney et al., *Modification Of Proteins; Advances in Chemistry Series*, vol. 198, American Chemical Society, Washington, D.C., 1982.

In certain embodiments, the cross-linking mechanism is one of the various forms of copper-free "click chemistry" reactions. In one embodiment, hydrogel formation by copper-free click chemistry comprises contacting a first predominantly hydrophilic polymer comprising at least two functional azide group moieties and a second predominantly hydrophilic polymer containing at least two functional alkyne group moieties, under conditions permitting the functional groups of the first polymer and the functional groups of the second polymer to react via a copper-free azide-alkyne cyclo-addition mechanism to form a cross-linked hydrogel. In another embodiment, hydrogel formation by a Michael-type addition reaction comprises contacting a first predominantly hydrophilic polymer comprising at least two functional alkene group moieties and a second predominantly hydrophilic polymer containing at least two functional reduced thiol group moieties in a manner that permits the functional groups of the first polymer and the functional groups of the second polymer to react via a Michael-type addition reaction mechanism to form a cross-linked hydrogel.

In certain embodiments, the reactive functional group is a member selected from a sulfhydryl group and a sulfhydryl-reactive group. Useful non-limiting examples of sulfhydryl-reactive groups include maleimides, alkyl halides, acyl halides (including bromoacetamide or chloroacetamide), pyridyl disulfides, and thiophthalimides. Maleimides react preferentially with the sulfhydryl group to form stable thioether succinimide bonds.

In preferred embodiments, the hydrogel comprises a cross-linked polymer network formed by reaction of a first base hydrophilic polymer comprising at least two first reactive functional groups, and a second base hydrophilic polymer comprising at least two second reactive functional groups that are reactive with the first reactive functional groups, to form the cross-linked polymer network. In preferred embodiments, at least some molecules of at least one of the first base hydrophilic polymer and the second base hydrophilic polymer comprise at least three reactive functional groups. Some or all molecules of either or both of the first and second base hydrophilic polymers may then comprise at least 4, 5, 6, or more respective reactive functional groups.

Examples of functionalized hydrogel-forming base polymers include, for example, dextran-hydroxyethylmethacrylate (DEX-HEMA), dextran-mono-2-(acryloyloxy)ethyl succinate (DEX-MAES), polyvinyl alcohol-mono-2-(acryloyloxy)ethyl succinate (PVA-MAES), n-arm-polyethylene glycol-mono-2-(acryloyloxy)ethyl succinate (n-arm-PEG-MAES), n-arm-polyethylene glycol-acrylate (n-arm-PEG-A), n-arm-polyethylene glycol-maleimide (n-arm PEG-MALEIMIDE), n-arm-polyethylene glycol-thiol (n-arm-PEG-SH), n-arm-polyethylene glycol-azide (n-arm-PEG-azide), and n-arm-polyethylene glycol-alkyne (n-arm-PEG-alkyne).

The value of "n" is preferably a value from 2 to 20, and is typically an even number (n=2, 4, 6, 8, 10, etc.). In certain embodiments, n is from 2 to 12, from 2 to 10, from 2 to 8, from 2 to 6, or from 2 to 4. In certain embodiments, n is 2, 4, 6, 8, 10, or 12. A preferred molecular weight of a functionalized hydrogel-forming base polymers is in the range of from about 5,000 to about 50,000 g/mol, more preferably from about 10,000 to about 40,000 g/mol. One preferred molecular weight is about 10,000 g/mol. Polymers larger than about 50,000 g/mol are possible.

The respective base polymer portions of the reactants may be the same or different. In certain embodiments, the polymers are selected from DEX, PEG, hyaluronic acid (HA), polypeptides, polysaccharides, and PVA.

In preferred embodiments, both base polymer portions comprise PEG, and the hydrogel comprises a hydrophilic polymer population having a first functionalized PEG species and a second functionalized PEG species, the first PEG species being at least partially cross-linked to the second PEG species.

In certain embodiments, the first PEG species comprises a reactive maleimide group and the second PEG species comprises a reactive thiol group, and the first PEG species and second PEG species are cross-linked by reaction of the maleimide and thiol groups to form thioether bonds. The first and second PEG species are preferably branched species having a branch count between two to twelve branch arms. In certain embodiments, the first and second PEG species have a molecular weight in the range of from about 5,000 to about 50,000 g/mol, more preferably from about 10,000 to about 40,000 g/mol. One preferred molecular weight is about 10,000 g/mol. PEG species larger than about 50,000 g/mol are possible. In certain embodiments, the first PEG species is 4-arm-PEG-MALEIMIDE and the second PEG species is 4-arm-PEG-SH. In certain embodiments, these PEG species have a molecular weight of about 10,000 g/mol. In certain embodiments, the PEG may be photopolymerized PEG, which may be unbranched.

The practice of the invention is illustrated by the following non-limiting examples.

Example 1

A. Assessment of Biocompatibility of Gel Components

Figure 1:
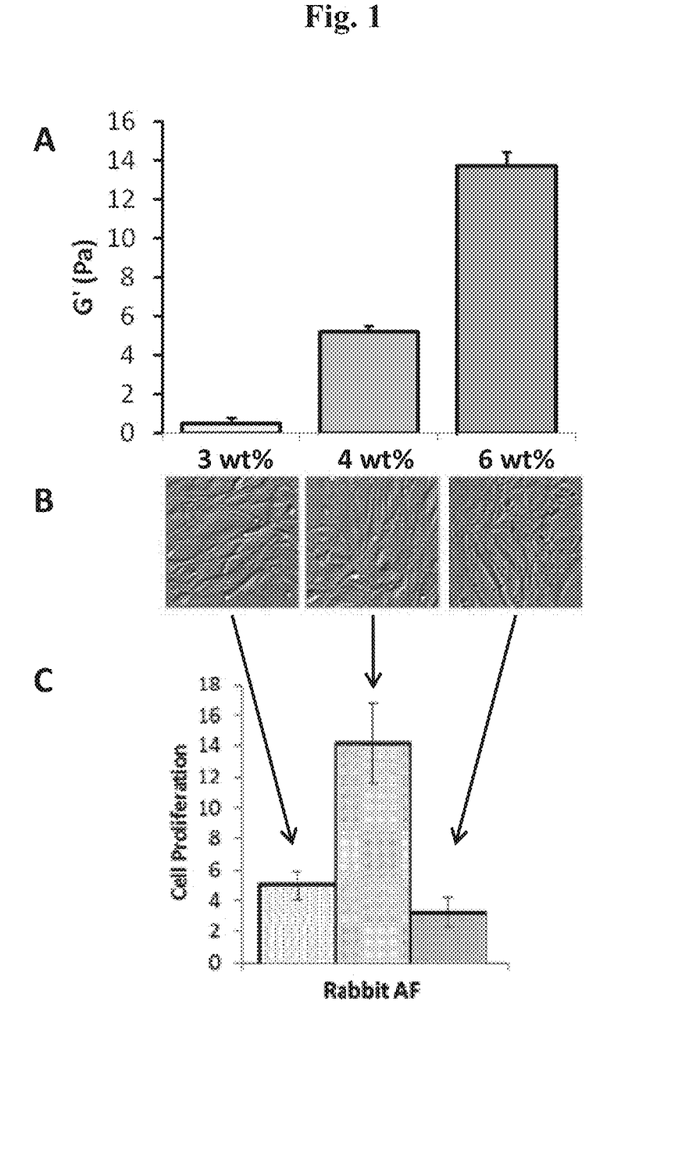
FIG. 1 shows a graph of the modulus (G') of 3 wt %, 4 wt %, and 6 wt % hydrogels prepared according to the present invention (A), the growth of primary rabbit aortic fibroblasts cultured on the 3 wt %, 4 wt % and 6 wt % hydrogels formulations (B), and a graph of the proliferation of rabbit aortic fibroblasts cultured on the 3 wt %, 4 wt %, and 6 wt % hydrogels formulations (C).

A solution of a maleimide-functionalized, "4-arm" polyethylene glycol (4-arm-PEG-MALEIMIDE (f=4, Mn 10,000 g/mol) having the structure and of a solution of a thiol-functionalized, "4-arm" polyethylene glycol (4-arm-PEG-SH) (f=4, Mn 10,000 g/mol) having the structure were obtained from JenKem Technologies USA, Plano, Tex. as hydrogel-forming components, employed to form gel networks. The biocompatibility of the gel components were assessed beforehand in cell culture using primary rabbit aortic fibroblasts. Cells grew well on multiple weight percentage (wt %) formulations (FIG. 1B) but exhibited a clear preference to proliferate on 4 wt % gels (FIG. 1C). Accordingly, 4 wt % gels were employed in the animal studies that follow. Gelation of the 4 weight percent (wt %) mixtures used in animals occurs in approximately 8 seconds with gels attaining a modulus (G') of approximately 3.5 kPa (FIG. 1A), which is similar to the reported modulus of stroma and smooth muscle (Cox and Erler, *Dis Model Mech* 4(2): 165-178, 2011).

B. Skeletonization and Hydrogel Formation.

Surgical procedures to skeletonize New Zealand white rabbit common carotid arteries were performed under an IACUC-approved protocol (NBR-2015-004) as follows. Twenty-four hours prior to surgery, analgesia (0.3 mg/kg meloxicam) was administered. Sixty minutes prior to surgery, cephazolin (50 mg/kg) was administered. Animals are anesthetized by IM injection of a cocktail of ketamine (35 mg/kg) and xylazine (5 mg/kg) into the paraspinal muscle or hind limb. An ear vein catheter was placed to allow IV delivery of additional doses of ketamine (35 mg/kg) and xylazine (5 mg/kg). Animals were placed on a warming blanket during the procedure. All instruments were sterilized by autoclave prior to use, and aseptic conditions were maintained in the operating area. Respiration, heart rate, and pO2 were continuously assessed and recorded at 10-minute intervals. The skin surface was cleaned with chlorhexidene and disinfected with alternating scrubs of 10% povidone-iodine (Betadine) and isopropyl alcohol, then thoroughly wiped with Betadine.

An approximately 4 cm incision was made on the left side of the trachea to expose the common carotid artery. The artery was skeletonized by carefully dissecting from surrounding tissue. A dose of heparin was given IV at least 3 minutes before placement of microvascular clips. Flow through the vessels was interrupted with microvascular clips for 5 minutes. Flow was re-established.

A sub-set of animals had hydrogel placed around the skeletonized vessel as follows. (Hydrogels were prepared in a sterile fashion with all components passing Limulus Amebocyte Lysate (LAL) assays prior to implantation.) 2 mM 4-arm-PEG-MALEIMIDE and 2 mM 4-arm-PEG-SH were separately dissolved in 10 mM citrate buffer, pH=6.1. Each component was sterilized by centrifugation through a 0.2-µm filter. Subsequently, 250 µl of each solution was mixed by double-barrel syringe equipped a mixing tip (Medmix Systems AG, Rotkreuz, Switzerland) to yield a 4-wt % hydrogel; changes in viscoelasticity were immediately apparent, and gelation was complete within 10 seconds. Stable hydrogel formed around the skeletonized artery. The common carotid artery of control animals was skeletonized according to the same protocol, but without hydrogel formation treatment. The incision was approximated with suture and the animals allowed to recover.

C. Artery Circumferential Cyclic Strain Analysis

Ultrasonography was performed on carotid arteries of all animals one day prior to surgery, immediately following surgery, and at intervals following surgery. Ultrasonography was performed using a VEVO® 2100 high-frequency, high-resolution, digital imaging system (VisualSonics Inc.) with a high frequency MicroScan transducer (Microscan Systems, Inc., Renton Wash.) to assess the operated and contralateral (i.e., control) carotids pre- and post-surgery, and then at intervals after surgery. High-resolution, two-dimensional cine loops in brightness mode (B-mode; 300 frames) and motion mode (M-mode; 3-5 second acquisition) were acquired of both the operated and contralateral carotid arteries in transverse view.

Circumferential cyclic strain values were calculated from M-mode diameter measurements. The distance between two lines of strong specular reflection seen in the anterior and posterior vessel walls was used to determine maximum (systolic) and minimum (diastolic) vessel diameter. Green-Lagrange circumferential strain was calculated from the ultrasound images using the following equation:

$$\text{Green-Lagrange Circumferential Cyclic Strain} = \left[\frac{1}{2}\left[\frac{D_S}{D_D}\right]^2 - 1\right] \times 100\%$$

In this context, the "strain" indicates the deformation of the vessel outwards under the influence of systolic versus diastolic blood pressure. More specifically, this is the mean maximum diameter during systole ($D_S$) divided by the mean minimum diameter during diastole ($D_D$) in the equation shown above.

Figure 2:
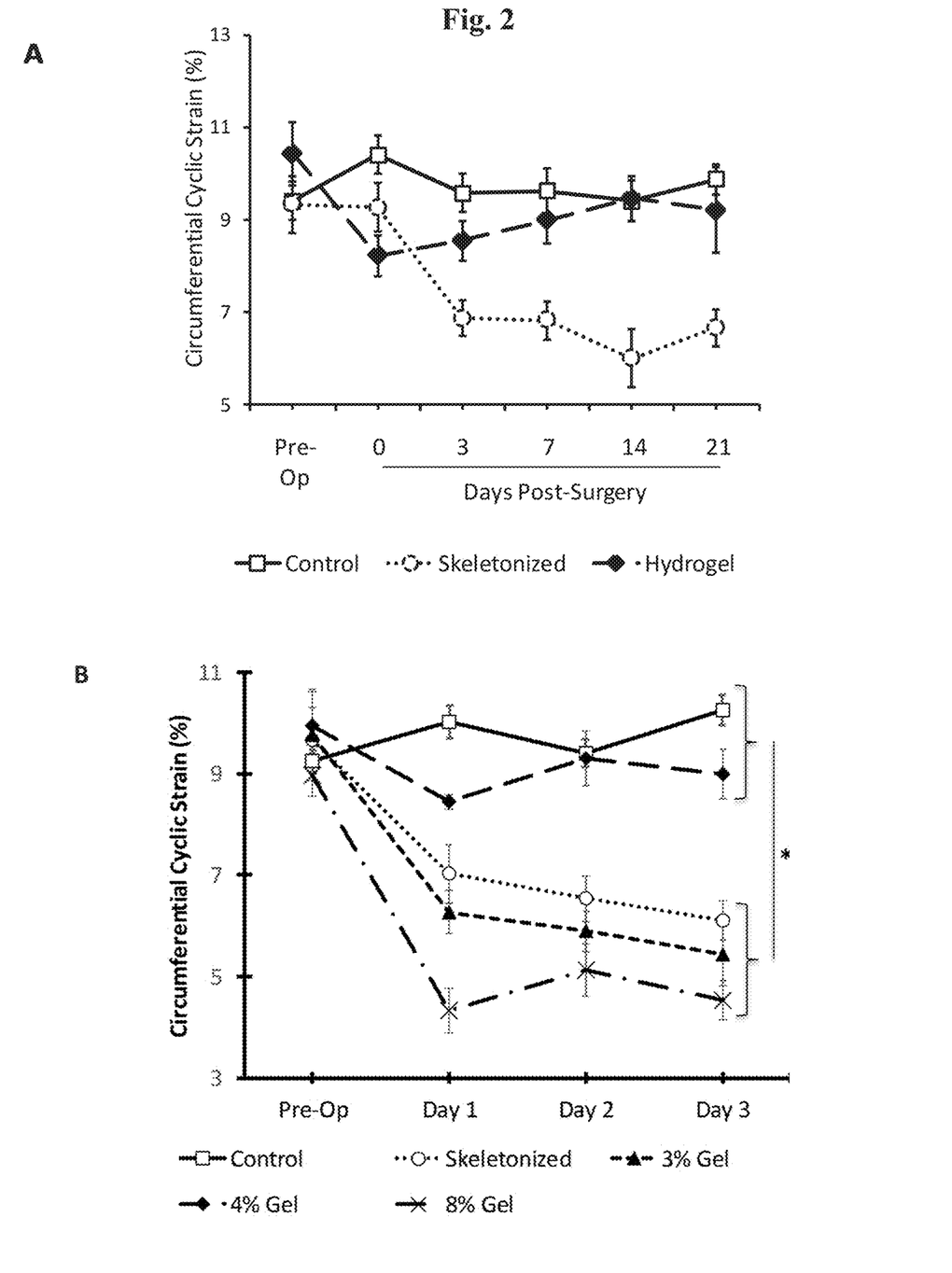
FIG. 2 shows plots of the circumferential cyclic strain (%) versus time (21 days) of unoperated control arteries (-□-; n=6), skeletonized arteries (-o-; n=3), and skeletonized arteries treated with 4 wt % hydrogel (-♦-; 3533±580 Pa; n=3) according to the present invention (A), and plots of circumferential cyclic strain of carotid arteries versus time (3 days) of unoperated control arteries (-□-; n=15), skeletonized arteries (-o-; n=5), and skeletonized arteries treated with 3 wt % hydrogel (-▲-; 752±52 Pa; n=3), 4 wt % hydrogel (-♦-; 3533±580 Pa; n=3), or 8 wt % hydrogel (-x-; 8613±544 Pa n=3) according to the present invention (B). For each study, high-frequency ultrasonography was performed on the arteries to determine circumfential cyclic strain. Skeletonization significantly decreased circumferential cyclic strain compared to unoperated controls. This effect persisted for 21 days. Treatment with 4% PEG hydrogel protected against this effect; however, treatment with 3% PEG hydrogel or 8% PEG hydrogel did not. * indicates $p<0.01$ by two-way ANOVA with post hoc Tukey HSD.

The results of FIG. 2 show the circumferential cyclic strain of unoperated control arteries (-□-), skeletonized arteries (-o-), and skeletonized arteries treated with 3 wt % hydrogel (-▲-), 4 wt % hydrogel (-▲-), or 8 wt % hydrogel (-x-) according to the present invention. The 4 wt % hydrogel protected the arteries from the decreased compliance seen after skeletonization. Application of 4 wt % hydrogel protected vessels from the alteration caused by skeletonization and allowed vessel elastic properties to return to control levels.

D. Intimal-Medial Thickness (IMT) Characterization

Animals were euthanized using a commercially available euthanasia agent (EUTHASOL® solution) containing a mixture of sodium pentobarbital (390 mg/ml) and sodium phenytoin (50 mg/ml), delivered intravenously using an ear-vein catheter to achieve a dose of at least 0.22 ml/kg. The skeletonized region of the operated left common carotid artery and the same anatomical region of the contralateral common carotid artery were harvested, fixed in 4% paraformaldehyde, and paraffin-embedded.

Figure 3:
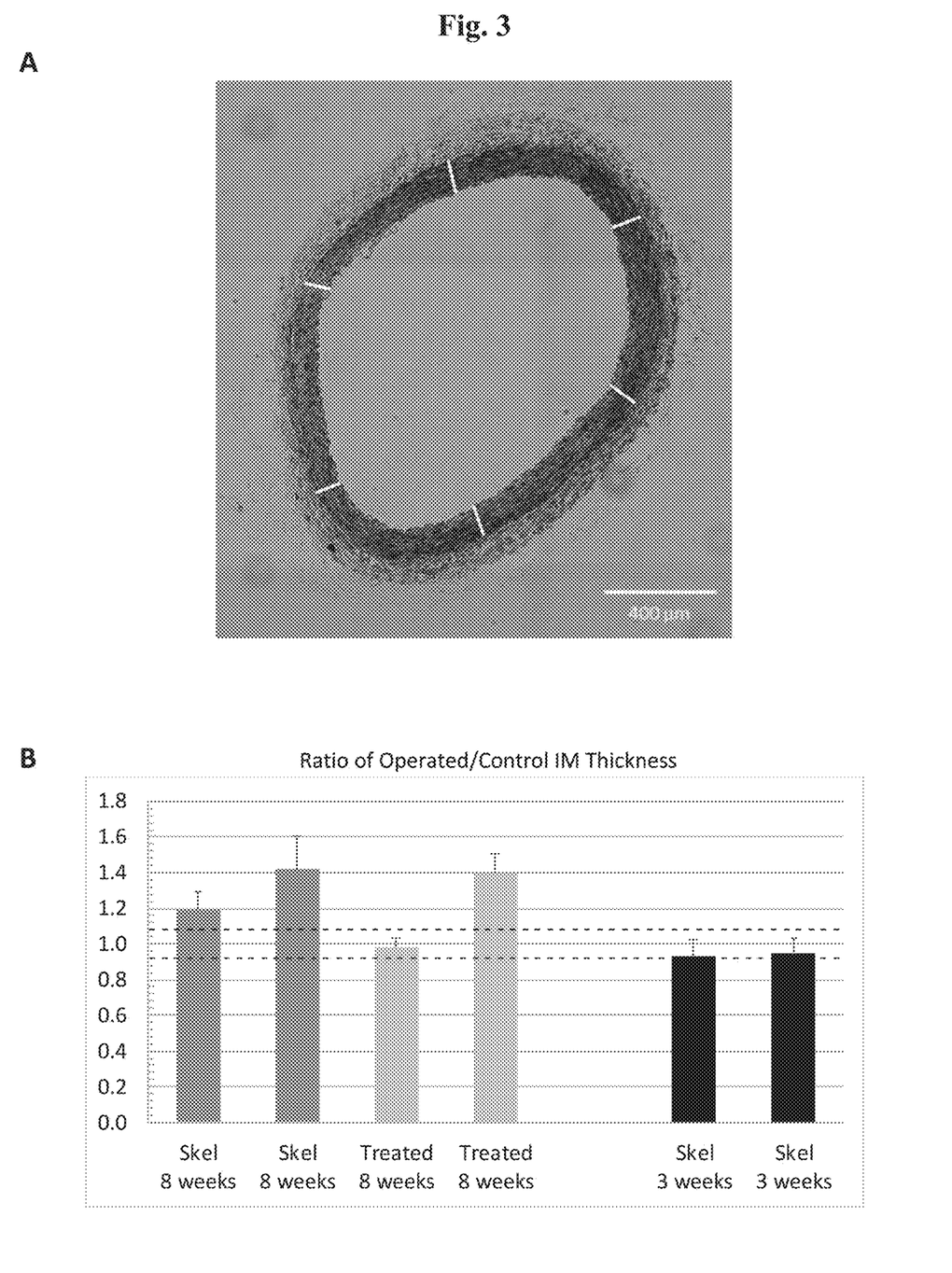
FIG. 3 shows a photomicrograph of a rabbit common carotid artery in cross section showing six regions delineated for intimal-medial thickness (IMT) analysis (A), and a graph of the ratio of the IMT of a skeletonized vessel divided by the IMT of the contralateral control artery for a series of 6 animals with skeletonized left common carotid arteries (B). Dashed lines indicate the range of ratios considered normal. Measurements were taken 3 or 8 weeks post-operation. From left to right are shown bars for skeletonized (8 weeks); skeletonized with non-hydrogel PEG exposure (8 weeks); skeletonized and treated with 1 ml of hydrogel (8 weeks); skeletonized and treated with 0.5 ml of hydrogel (8 weeks); skeletonized (3 weeks); and skeletonized (3 weeks). Values represent ±standard error of the mean. IM thickness ratios remained in the normal range at 3 weeks post skeletonization. The skeletonized tissue treated with 1 ml of hydrogel retained an IM thickness ratio within the normal range; whereas, the other arteries (untreated and treated with only 0.5 ml of hydrogel) showed IM thickness increases indicative of hyperplasia.

Tissue collected after euthanasia was characterized to determine intimal-medial thickness (IMT) using histologically stained tissue sections. Transverse carotid artery sections (5 μm) were stained with hematoxylin and eosin and imaged on an EVOS® FL Imaging System (Thermo Fisher Scientific Inc.). For each sample, intima-media thickness (IMT) was measured in six regions of the artery shown in cross section in FIG. 3A using IMAGE PRO® Plus Rockville, Md.) software.

Table 1 provides a summary of IMT measures for a series of 6 animals with skeletonized left common carotid arteries: MZ, 7, and 8 were received no hydrogel; MZ2 received hydrogel components, but no gel was formed; MZ4 and 5 received hydrogel as indicated.

TABLE 1

| Sample | Group | Study length | Control Carotid Artery IMT (μm) | Operated Carotid Artery IMT (μm) |
|---|---|---|---|---|
| MZ1 | Skeletonized | 8 weeks | 97.6 ± 11.0 | 116.3 ± 11.8 |
| MZ2 | Skeletonized; non-hydrogel PEG exposure | 8 weeks | 102.7 ± 21.4 | 145.6 ± 16.3 |
| MZ4 | Skeletonized; hydrogel (1 ml) treated | 8 weeks | 122.2 ± 4.9 | 119.7 ± 12.1 |
| MZ5 | Skeletonized; hydrogel (0.5 ml) treated | 8 weeks | 138.1 ± 16.2 | 193.3 ± 12.8 |
| MZ7 | Skeletonized | 3 weeks | 140.2 ± 9.2 | 131.1 ± 23.5 |
| MZ8 | Skeletonized | 3 weeks | 134.1 ± 15.5 | 127.0 ± 14.9 |

Although skeletonized vessels showed no increase in IMT after 3 weeks (MZ7, MZ8), skeletonization resulted in a significant increase in IMT after 8 weeks in two animals that were taken to that point (MZ1, MZ2). Additionally, in two cases taken to eight weeks, hydrogel was placed immediately after skeletonization (MZ4, MZ5); in these, the IMT remained at control levels in one animal (MZ4) suggesting the hydrogel treatment protected the blood vessel in at least one of the two cases completed to-date.

FIG. 3B shows the ratio of skeletonized (operated) vessel divided by the IMT of the contralateral control for each animal (+summed Standard Error of the Mean). The dashed lines indicate the estimated range for control vessels.

E. Elastin and Collagen Analysis

Tissue collected after euthanasia was further characterized to determine elastin and collagen composition using multiphoton microscopy. The multiphoton microscopy approach employed combined two photon autofluorescence from elastin and second harmonic generation from collagen as described by Ghazanfari, et al., Biochem Biophys Res Commun 426(1): 54-58 (2012). This approach allows the visualization of collagen and elastin in unstained samples. Elastin and collagen were visualized in paraffin-embedded sections using a Zeiss LSM 780 confocal microscope with a 3-watt Chameleon Vision II multiphoton laser at 820 nm (Coherent Inc., Santa Clara, Calif.). Elastin autofluorescence was visualized and a non-descanned detector (NDD) system was used for detection of second harmonic generation (SHG) in the forward and reverse directions to visualize collagen.

Figure 4:
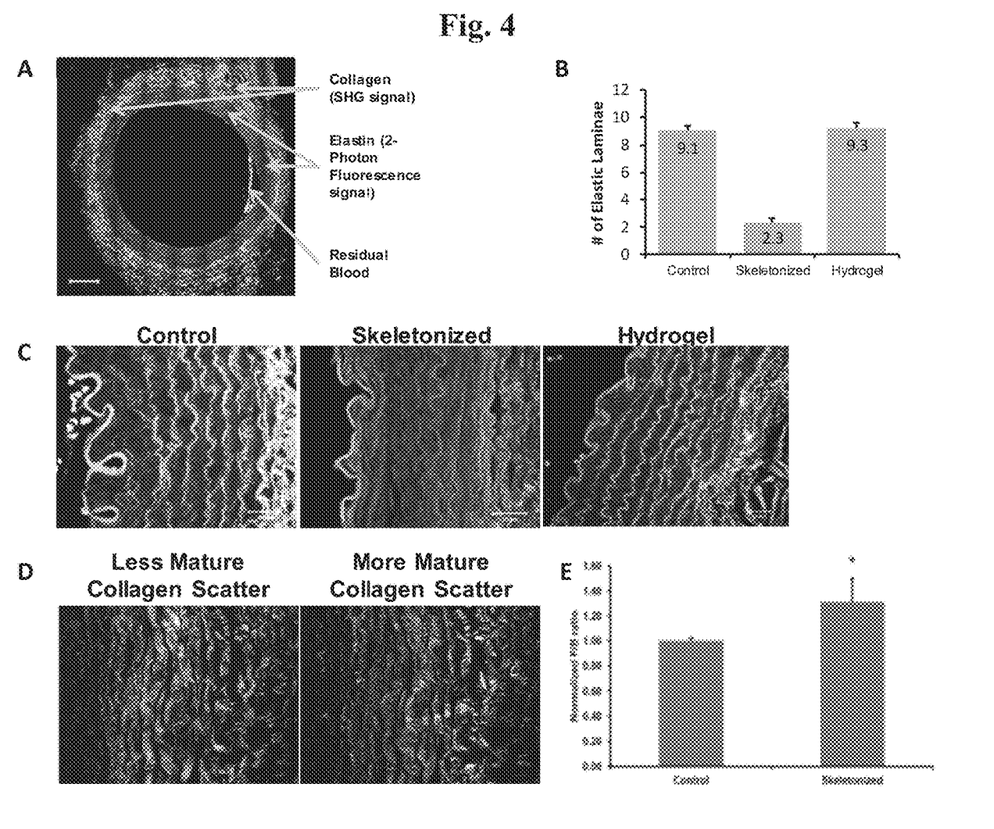
FIG. 4 shows the combined two-photon autofluorescence of elastin (shown in yellow in the original color image) and second harmonic generation signals from collagen (cyan and magenta in the original color image) showing the distribution of signal in a normal carotid (A). In this representation, collagen is represented by two signals (forward scatter in magenta and backward scatter in cyan in the original color image) and blood is displayed in the same color channel as elastin.

FIG. 4A shows combined two-photon autofluorescence of elastin (yellow in color images; indicated by arrows) and second harmonic generation signal from collagen (cyan in color images; indicated by arrows) showing the distribution of signal in a carotid artery. In this representation, the collagen is represented by two signals (forward and backward scatter) and the blood is displayed in the same color channel as elastin. There are also indications from the second harmonic generation (SHG) signals that the collagen organization is altered (FIG. 4E).

FIG. 4B is a graph of the number of elastic laminae present in sections of carotid from control, skeletonized, and skeletonized hydrogel-treated arteries. The three panels of FIG. 4C show examples of elastin distribution patterns from the control, skeletonized and hydrogel-treated vessels. Elastin organization in the skeletonized vessels degrades and the number of intact elastic laminae decreases. The placement of hydrogel around vessels just after skeletonization protected the elastic components from the effects of skeletonization.

Forward and backward scatter second harmonic signals from collagen were used to form an image wherein mature collagen appears magenta and newer collagen appears yellow. Differences in the back versus forward patterns are indicative of new collagen formation and collagen turnover. The results are shown in FIG. 4D and FIG. 4E.

F. Discussion

Skeletonization results in a decrease in the circumferential strain seen in carotid arteries. This decrease occurs within 72 hours after surgery and is sustained for at least 3 weeks. Application of hydrogel abrogates the effects of skeletonization. In a small number of animals, skeletonization was associated with an increase in IMT at 8 weeks post procedure. In one of two animals, hydrogel diminished this hypertrophic/atherosclerotic response. Skeletonization reduced the appearance of medial elastin and reduced the number of intact elastic laminae. Application of hydrogel blocked this effect. In addition, there may be effects on collagen organization associated with skeletonization.

The disclosures of each and every patent, patent application, GenBank record, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope used in the practice of the invention. The appended claims are intended to be construed to include all such embodiments and equivalent variations.

We claim:

1. A method for protecting a skeletonized blood vessel, comprising forming a coating on at least a portion of an outer surface of the skeletonized blood vessel, wherein the coating comprises a biocompatible hydrogel.

2. The method of claim 1, wherein the blood vessel is a vein.

3. The method of claim 1, wherein the blood vessel is an artery.

4. The method of claim 1, wherein the blood vessel is selected from the group consisting of aortas, carotid arteries, coronary arteries, internal mammary arteries, internal thoracic arteries, radial arteries, femoral arteries, gastroepiploic arteries, popliteal arteries, and saphenous veins.

5. The method of claim 4, wherein the blood vessel is a saphenous vein.

6. The method of claim 1, wherein the skeletonized blood vessel is harvested from a donor, further comprising depositing the coating on the outer surface of the skeletonized blood vessel in the donor before harvesting.

7. The method of claim 1, further comprising delivering to the outer surface a composition comprising two or more hydrogel precursor reactants, whereby the two or more hydrogel precursor reactants react and form the coating on the outer surface.

8. The method of claim 1, wherein the hydrogel comprises a cross-linked polymer network formed by reaction of a first functionalized base polymer comprising at least two first reactive groups and a second functionalized base polymer comprising at least two second reactive groups, the second reactive groups being reactive with the first reactive groups, thereby forming the cross-linked polymer network.

9. The method of claim 1, wherein the hydrogel has a modulus of from about 600 Pa to 13,000 Pa.

10. The method of claim 1, wherein the cross-linked polymer network comprises a heterogeneous component.

11. The method of claim 8, wherein the first reactive groups comprise maleimide moieties, and wherein the second reactive groups comprise thiol moieties.

12. The method of claim 8, wherein the first and second functionalized base polymers are selected from the group consisting of polyethylene glycol, poly(ethylene oxide), poly(vinyl alcohol), poly(N-alkyl acrylamide)s, poly(ester)s, poly(N-vinylpyrrolidone), poly(vinyl acetate), proteins, polypeptides, peptides, polysaccharides, and copolymers, conjugates or mixtures thereof.

13. The method of claim 12, wherein the first and second functionalized base polymers comprise functionalized polyethylene glycol.

14. The method of claim 13, wherein the first functionalized base polymer comprises $n_1$-arm-PEG-MALEIMIDE, wherein $n_1$ is an integer from 2 to 12, and wherein the second functionalized base polymer comprises $n_2$-arm-PEG-SH wherein $n_2$ is an integer from 2 to 12.

15. A method for harvesting a skeletonized blood vessel from a donor, comprising exposing a blood vessel in a donor, skeletonizing the exposed blood vessel, and forming a coating comprising a biocompatible hydrogel on at least a portion of an outer surface of the exposed skeletonized blood vessel.

16. A skeletonized blood vessel coated with a biocompatible hydrogel on at least a portion of an outer surface of the skeletonized blood vessel.

17. The skeletonized blood vessel of claim 16, wherein the skeletonized blood vessel is harvested from a donor.

18. The method of claim 1, wherein the hydrogel is deployed only on the outer surface and around the circumference of the skeletonized blood vessel.

19. The method of claim 1, further comprising delivering to the outer surface a composition comprising two or more hydrogel precursor reactants, whereby the two or more hydrogel precursor reactants react and form the coating on the outer surface, and wherein the hydrogel has a modulus of from about 600 Pa to 13,000 Pa.

20. The method of claim 15, further comprising delivering to the outer surface a composition comprising two or more hydrogel precursor reactants, whereby the two or more hydrogel precursor reactants react and form the coating on the outer surface, and wherein the hydrogel has a modulus of from about 600 Pa to 13,000 Pa.

* * * * *